(12) United States Patent
Nakayama et al.

(10) Patent No.: US 12,398,414 B2
(45) Date of Patent: Aug. 26, 2025

(54) BIOLOGICAL SAMPLE ANALYSIS APPARATUS AND BIOLOGICAL SAMPLE ANALYSIS METHOD

(71) Applicant: HORIBA Advanced Techno, Co., Ltd., Kyoto (JP)

(72) Inventors: Hideki Nakayama, Kyoto (JP); Yoko Nakai, Kyoto (JP); Masanori Kido, Kyoto (JP); Kazuya Nakagawa, Kyoto (JP)

(73) Assignee: HORIBA ADVANCED TECHNO, CO., LTD., Kyoto (JP)

( * ) Notice: Subject to any disclaimer, the term of this patent is extended or adjusted under 35 U.S.C. 154(b) by 664 days.

(21) Appl. No.: 17/595,825

(22) PCT Filed: Jun. 29, 2020

(86) PCT No.: PCT/JP2020/025461
§ 371 (c)(1),
(2) Date: Nov. 24, 2021

(87) PCT Pub. No.: WO2021/002311
PCT Pub. Date: Jan. 7, 2021

(65) Prior Publication Data
US 2022/0228191 A1   Jul. 21, 2022

(30) Foreign Application Priority Data

Jul. 2, 2019  (JP) ................................. 2019-123883

(51) Int. Cl.
*C12Q 1/04*  (2006.01)
*B01L 3/00*  (2006.01)
(Continued)

(52) U.S. Cl.
CPC .............. *C12Q 1/04* (2013.01); *B01L 3/5025* (2013.01); *G01N 21/76* (2013.01); *G01N 35/028* (2013.01);
(Continued)

(58) Field of Classification Search
CPC ... C12Q 1/04; B01L 3/5025; B01L 2200/025; B01L 2200/10; B01L 2200/16;
(Continued)

(56) References Cited

U.S. PATENT DOCUMENTS 4,349,510 A * 9/1982 Kolehmainen .. G01N 35/00009
435/808
2002/0068338 A1 * 6/2002 Nanda .................... C12M 35/02
435/173.6
(Continued)

FOREIGN PATENT DOCUMENTS

CN        101290294 A    10/2008
CN        102326087 A    1/2012
(Continued)

OTHER PUBLICATIONS

European Patent Office, Supplementary European Search Report Issued in Application No. 20835581.8, Dec. 5, 2022, Germany, 13 pages.
(Continued)

*Primary Examiner* — Jill A Warden
*Assistant Examiner* — Jacqueline Brazin
(74) *Attorney, Agent, or Firm* — Alleman Hall & Tuttle LLP (57) ABSTRACT

In order to provide a biological sample analysis apparatus capable of preventing a container storing a sample from being charged and of measuring only a luminescence intensity of light emitted from the sample accurately, a biological sample analysis apparatus for rapid microbiological test
(Continued)

analyzes light generated from a biological origin substance contained in a sample, and includes a holder that holds a plurality of containers storing the sample, a photodetector fixed at a predetermined position, a holder drive mechanism that drives the holder and sequentially positions each of the containers held by the holder at a detection position detected by the photodetector, and a neutralizer that neutralizes the containers held by the holder.

12 Claims, 8 Drawing Sheets

(51) Int. Cl.
  *G01N 21/76* (2006.01)
  *G01N 35/02* (2006.01)
  *G01N 35/04* (2006.01)
  *G01N 35/10* (2006.01)

(52) U.S. Cl.
  CPC .... *G01N 35/1002* (2013.01); *B01L 2200/025* (2013.01); *B01L 2200/10* (2013.01); *B01L 2200/16* (2013.01); *B01L 2300/0609* (2013.01); *B01L 2300/0663* (2013.01); *B01L 2300/168* (2013.01); *B01L 2300/1827* (2013.01); *G01N 2035/0496* (2013.01)

(58) Field of Classification Search
  CPC ..... B01L 2300/0609; B01L 2300/0663; B01L 2300/168; B01L 2300/1827; G01N 21/76; G01N 35/028; G01N 35/1002; G01N 2035/0496; G01N 21/0332; G01N 2035/00346; G01N 2035/00495; G01N 2035/0441; G01N 2201/0415; G01N 2201/064; G01N 21/253; G01N 21/763; G01N 35/00; G01N 35/04

USPC ....................................................... 435/283.1
  See application file for complete search history.

(56) References Cited

U.S. PATENT DOCUMENTS

| | | | |
|---|---|---|---|
| 2007/0116444 A1* | 5/2007 | Brown | B01L 7/52 392/467 |
| 2012/0114526 A1 | 5/2012 | Watanabe et al. | |
| 2019/0170778 A1 | 6/2019 | Kitamura | |
| 2020/0110033 A1 | 4/2020 | Nakagawa et al. | |

FOREIGN PATENT DOCUMENTS

| | | | | |
|---|---|---|---|---|
| CN | 109580593 | * | 9/2017 | |
| CN | 109580593 | A | 4/2019 | |
| JP | 2001004640 | A | 1/2001 | |
| JP | 2006162251 | A | 6/2006 | |
| JP | 2006275820 | A | 10/2006 | |
| JP | 2008268019 | A | 11/2008 | |
| JP | 2019100894 | A | 6/2019 | |
| WO | WO-2006126285 A1 | * | 11/2006 | ......... G01R 19/0061 |
| WO | 2019013360 A1 | | 1/2019 | |

OTHER PUBLICATIONS

ISA Japan Patent Office, International Search Report Issued in Application No. PCT/JP2020/025461, Sep. 15, 2020, WIPO, 4 pages.
China National Intellectual Property Administration, Office Action and Search Report Issued in Application No. 202080038474.9, Nov. 9, 2023, 17 pages.
Japan Patent Office, Office action issued in Japanese Application No. 2021-530006, Nov. 14, 2024, 6 pages.

* cited by examiner

BIOLOGICAL SAMPLE ANALYSIS APPARATUS AND BIOLOGICAL SAMPLE ANALYSIS METHOD

TECHNICAL FIELD

The present invention relates to a biological sample analysis apparatus that analyzes light generated by a biological origin substance contained in a sample.

BACKGROUND ART

Conventionally, microbial monitoring has been performed for environmental management of pharmaceutical production plants, food plants, and the like. As an example of this microbial monitoring, a luminescent reagent is added to adenosine triphosphate (ATP) contained in a microorganism, bioluminescence of the luminescent reagent is measured, an obtained luminescence intensity is converted into an ATP value, and thus correlation with bacterium can be taken.

As a device that analyzes light generated by a biological origin substance such as ATP, a device disclosed in Patent Literature 1 is considered. This biological sample analysis apparatus includes a holder that holds a single container accommodating a sample, and a light-shielding box that accommodates a photodetector, in which the holder is installed in the light-shielding box, and light emitted from the sample in the container is detected.

The luminescence intensity due to bioluminescence, which is a significantly minute value, needs to be measured with a photodetector such as a photomultiplier tube (PMT) having significantly high sensitivity. Therefore, when the container storing the sample is charged by friction or the like, light due to static discharge may be detected by the photodetector and appear as a measurement error.

CITATION LIST

Patent Literature

Patent Literature 1: JP 2008-268019 A

SUMMARY OF INVENTION

Technical Problem

The present invention has been made in view of the above problem, and an object of the present invention is to provide a biological sample analysis apparatus capable of preventing a container storing a sample from being charged and of measuring only a luminescence intensity of light emitted from the sample accurately.

Solution to Problem

A biological sample analysis apparatus for rapid microbiological test of the present invention analyzes light generated by a biological origin substance contained in a sample, the biological sample analysis apparatus including a holder that holds a plurality of containers storing the sample, a photodetector fixed at a predetermined position, a holder drive mechanism that drives the holder and sequentially positions each of the containers held by the holder at a detection position detected by the photodetector, and a neutralizer that neutralizes the containers held by the holder.

A biological sample analysis method of the present invention uses a biological sample analysis apparatus for rapid microbiological test, the biological sample analysis apparatus analyzing light generated by a biological origin substance contained in a sample, in which the biological sample analysis apparatus includes a holder that holds a plurality of containers storing the sample, a photodetector fixed at a predetermined position, and a holder drive mechanism that drives the holder and sequentially positions each of the containers held by the holder at a detection position detected by the photodetector, the method comprising neutralizing the containers held by the holder.

In such a configuration, the containers, which are charged for some reason, can be neutralized by the neutralizer, and thus, it is possible to prevent light due to discharge from being detected by the photodetector due to static electricity generated by charging the containers. Therefore, only light generated by a biological origin substance in the containers can be detected by the photodetector.

In addition, the neutralization of the containers makes it difficult for droplets of the sample to adhere to a wall surface of each container, and this reduces an amount of the sample that does not react with the reagent and prevents occurrence of a measurement error.

In order for the photodetector to be less affected by a neutralization action itself on the containers by the neutralizer, it is sufficient that the holder is rotatable about a predetermined rotation center and holds the plurality of containers on an identical circumference about the rotation center, and the neutralizer is disposed apart from the photodetector by a predetermined arc length in a circumferential direction in which the plurality of containers are arranged.

Specific aspects of the neutralizer include the neutralizer supplying positive ions and negative ions to the containers.

In order to sufficiently neutralize a part of the containers close to the photodetector so as not to be affected by charging, it is sufficient that each of the containers has a substantially tubular shape and has a distal end that is exposed downward from the holder, and the neutralizer supplies positive ions and negative ions from below the containers.

In order to prevent the holder itself from being charged and light due to discharge from being detected by the photodetector to cause a measurement error, it is sufficient that the holder includes a conductor.

In order to release the electric charge charged in the containers or the holder to outside, it is sufficient that the holder is electrically connected to the holder drive mechanism and connected to a ground.

Specific configuration examples for releasing the electric charge charged in the containers or the holder to the ground include a configuration in which the holder drive mechanism includes a rotation shaft connected to the holder and further includes a ground member that clamps a side surface of the rotation shaft. In this configuration, contact between the rotation shaft and the ground member is easily maintained by elasticity of the ground member when wear occurs therebetween.

In order to prevent the container from being charged by a member related to a process before the sample is stored in each of the containers and being charged through a transfer of the sample, it is sufficient to further include a dispensing mechanism that introduces, into the containers, a reagent that reacts with the biological origin substance and generates light, in which the dispensing mechanism is attachable to and detachable from a pipette tip that is in contact with the reagent, and the pipette tip is wet before being used. This configuration can make the pipette tip less likely to be charged and prevent the containers from being charged while the sample is transferred.

In order to prevent occurrence of a measurement error due to charging of a member for light shielding while shielding light such that light from outside does not enter the detector when light emission from the sample is detected by the photodetector, it is sufficient to further include a light shielding mechanism provided on each of the containers and including a container-side light shield that covers an upper part of each of the containers and a movable-side light shield that moves forward and backward with respect to each of the containers located at the detection position and covers a lower part of each of the containers located at the detection position, in which the container-side light shield and the movable-side light shield include metal.

In order to easily perform cleaning and the like to prevent the light emission from the sample from being shielded when water droplets accumulate in the light shielding mechanism, it is sufficient that the movable-side light shield includes a reflector body that covers a distal end of each of the containers, a light transmitting plate provided in the reflector body, and a pressing member that is attachable to and detachable from the reflector body and presses and fixes the light transmitting plate to the reflector body.

In order to prevent light emission from the sample from being absorbed by the pressing member and a measurement error from occurring, it is sufficient that the pressing member has a substantially ring shape attached in the reflector body and has an inner peripheral surface provided with a reflective film.

In order to reduce an error in an installation position of a thermistor to adjust temperature accurately for maintaining a constant state of the sample before measurement, it is sufficient to further include a temperature control mechanism including a holder block that holds a specimen tube storing the sample before being dispensed into the containers, and a heat source provided in the holder block, a thermistor that includes a temperature sensor and a lead wire connected to the temperature sensor and measures a temperature of the holder block, an accommodating hole provided in the holder block and configured to accommodate the thermistor inside, and an insertion body that covers a lead wire of the thermistor and is inserted into the accommodating hole, in which the insertion body has an abutment surface that abuts on a periphery of an opening of the accommodating hole at a base end of the insertion body.

Advantageous Effects of Invention

As described above, in the biological sample analysis apparatus of the present invention, the containers are neutralized by the neutralizer, and it is therefore possible to prevent the containers from being charged and light due to static discharge from being detected by the photodetector. This makes it possible to measure only the light from the sample and thus to measure a significantly low luminescence intensity accurately.

LIST OF REFERENCE CHARACTERS 100 biological sample analysis apparatus
Xdet detection position
2 container
3 holder
4 photodetector
NE neutralizer
5 holder drive mechanism
6 dispensing mechanism
11 reflector
13 light shielding mechanism
131 container-side light shield
132 movable-side light shield

DESCRIPTION OF EMBODIMENT

Hereinafter, an embodiment of a biological sample analysis apparatus of the present invention will be described with reference to the drawings.

<Device Configuration>

A biological sample analysis apparatus 100 for rapid microbiological test according to the embodiment analyzes light generated by a biological origin substance contained in a sample to measure an amount of the biological origin substance. In other words, the biological sample analysis apparatus 100 according to the embodiment is a biological sample analysis apparatus for a highly sensitive microbiological test, and is intended for measurement in which a count number of photons is 1,000 counts or less per second, for example. In the embodiment, 30 counts to 100 counts per second are set as 0 points, and measurement in which a difference in number counts corresponds to an abundance of one bacterium is intended. In the following, an ATP amount measurement device that measures an amount of adenosine triphosphate (ATP) (amol ($=10^{-18}$ mol)) as a biological origin substance by detecting weak light generated from ATP will be described.

Figure 1:
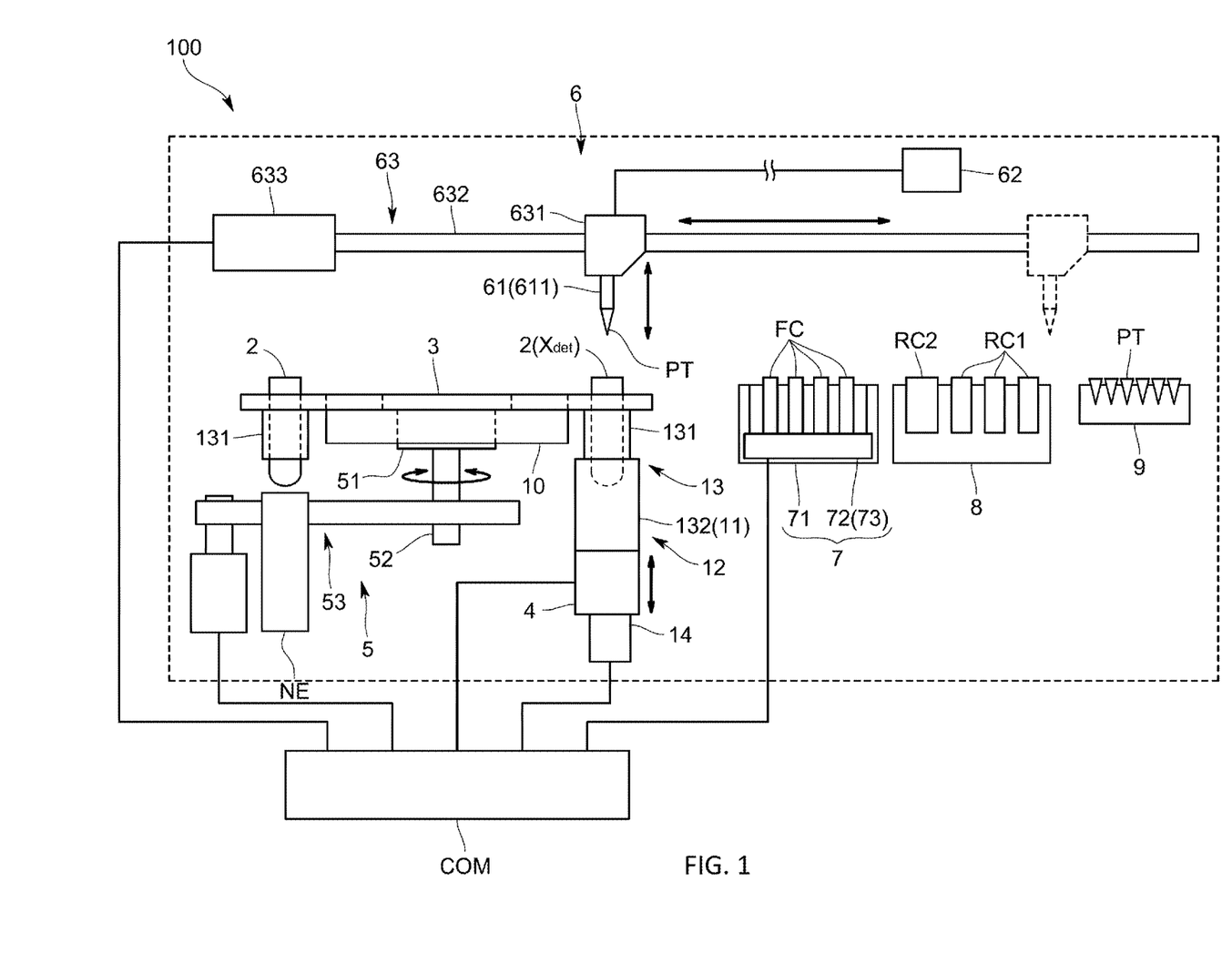
FIG. 1 is a schematic diagram illustrating a configuration of a biological sample analysis apparatus according to an embodiment.

Specifically, as illustrated in FIG. 1, the biological sample analysis apparatus 100 includes a holder 3 that holds a plurality of containers 2 containing a sample, a photodetector 4 fixed at a predetermined position, a holder drive mechanism 5 that moves the holder 3, and a dispensing mechanism 6 that dispenses a luminescent reagent that reacts with ATP to generate light into the containers 2 held by the holder 3.

Figure 2:
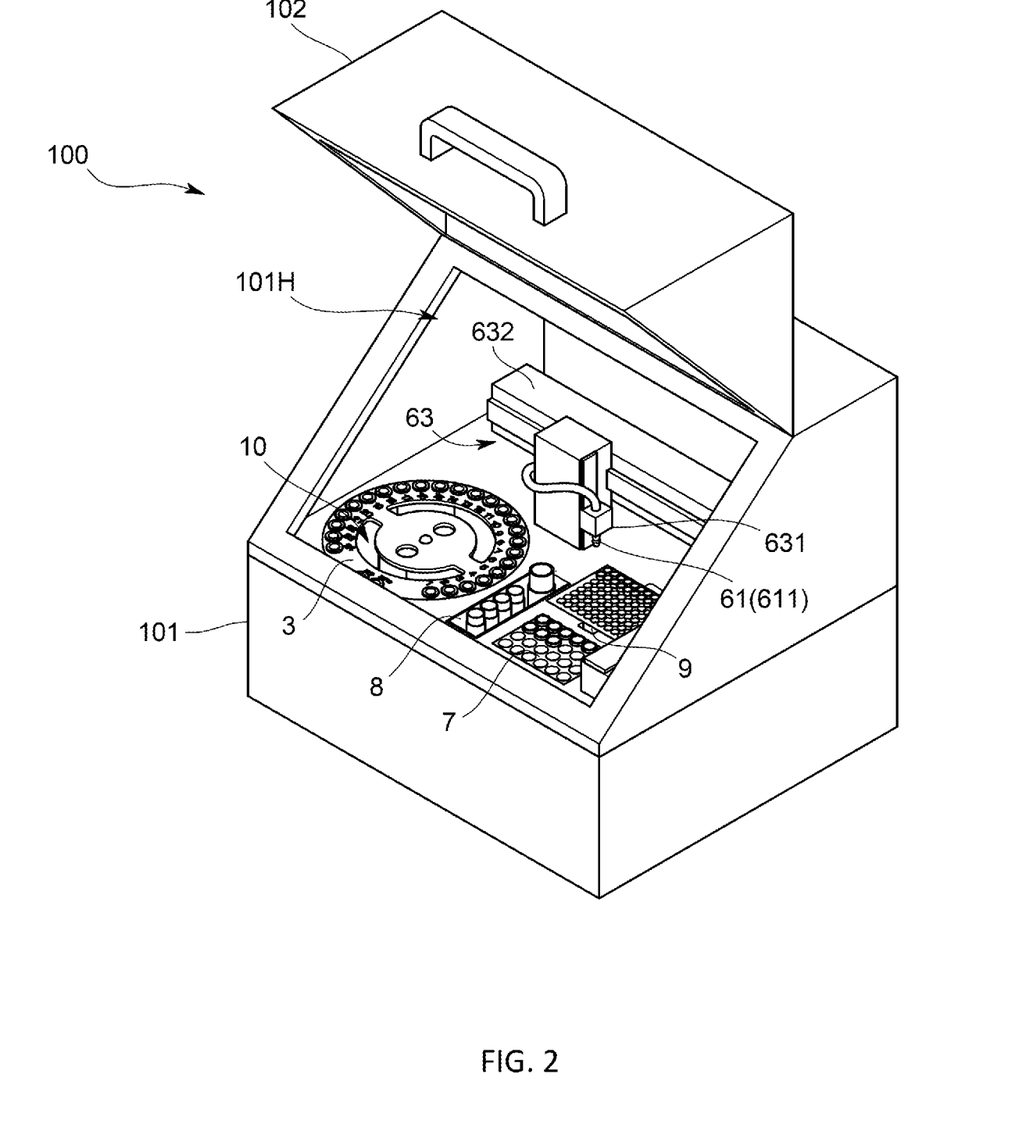
FIG. 2 is a perspective view illustrating an appearance of the biological sample analysis apparatus according to the embodiment.
Figure 3:
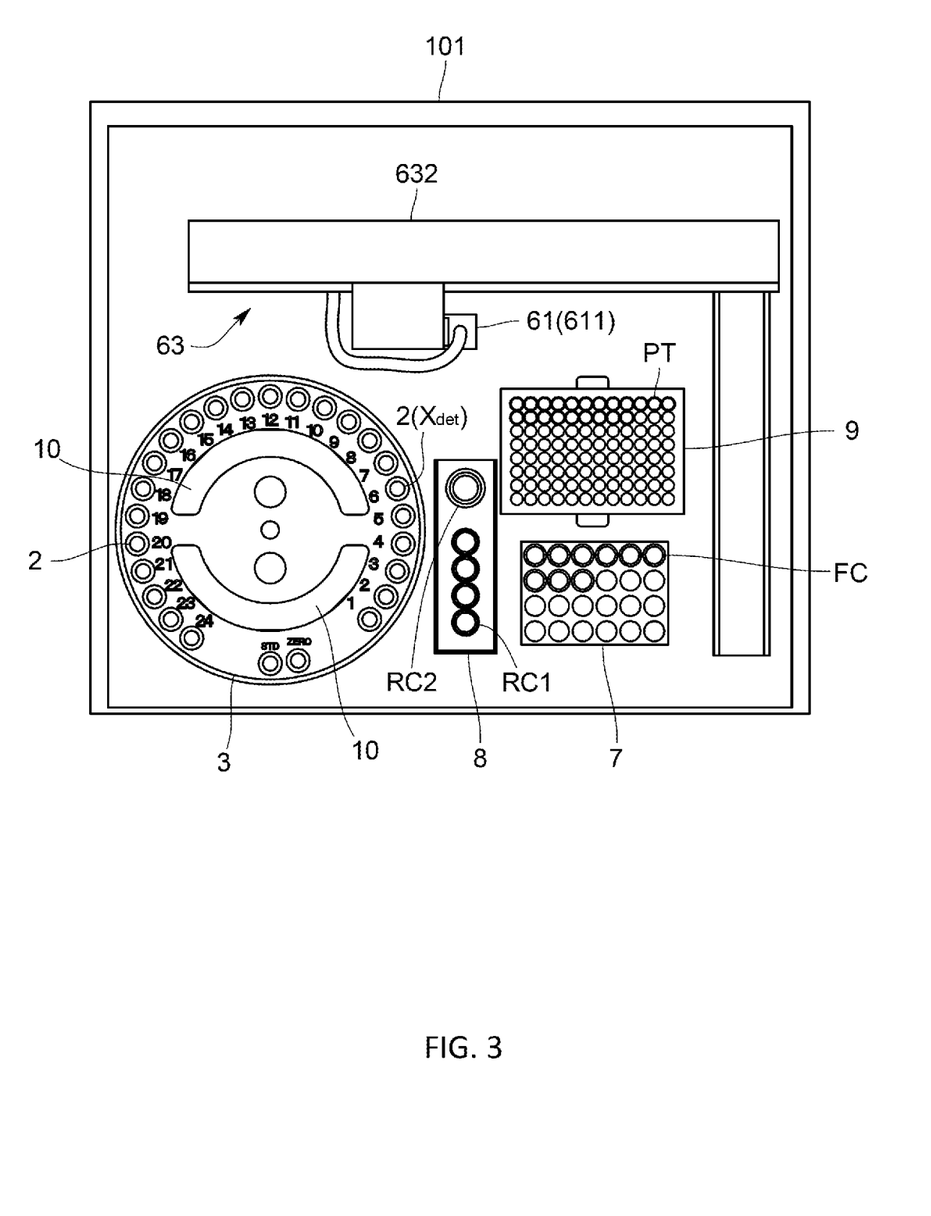
FIG. 3 is a plan view illustrating an arrangement of components of a device body according to the embodiment.

As shown in FIGS. 2 and 3, the biological sample analysis apparatus 100 according to the embodiment includes a device body 101 placed on a stage such as a clean bench, and a cover 102 provided on the device body 101. The device body 101 is provided with measurement system instruments necessary for ATP measurement, such as the holder 3, the holder drive mechanism 5, and the dispensing mechanism 6. The device body 101 has an opening 101H on a front surface. The cover 102 is configured to open and close the opening 101H of the device body 101. Specifically, an upper part of the opening 101H is openable and closable by a horizontal coupling shaft (not illustrated), and a user can access inside of the device body 101 by lifting the cover 102 upward. Note that, in a state where the cover 102 is closed, a space between the cover 102 and the opening 101H is sealed by a seal member (not illustrated), and the inside of the device becomes a dark room.

Further, the device body 101 is provided with a temperature control mechanism 7 that holds a plurality of specimen tubes FC containing specimens and adjusts temperature of the specimen tubes FC, a reagent setting part 8 in which reagent containers RC1 and RC2 containing reagents are set, and a pipette tip setting part 9 provided with a pipette tip PT used for the dispensing mechanism 6.

Figure 4:
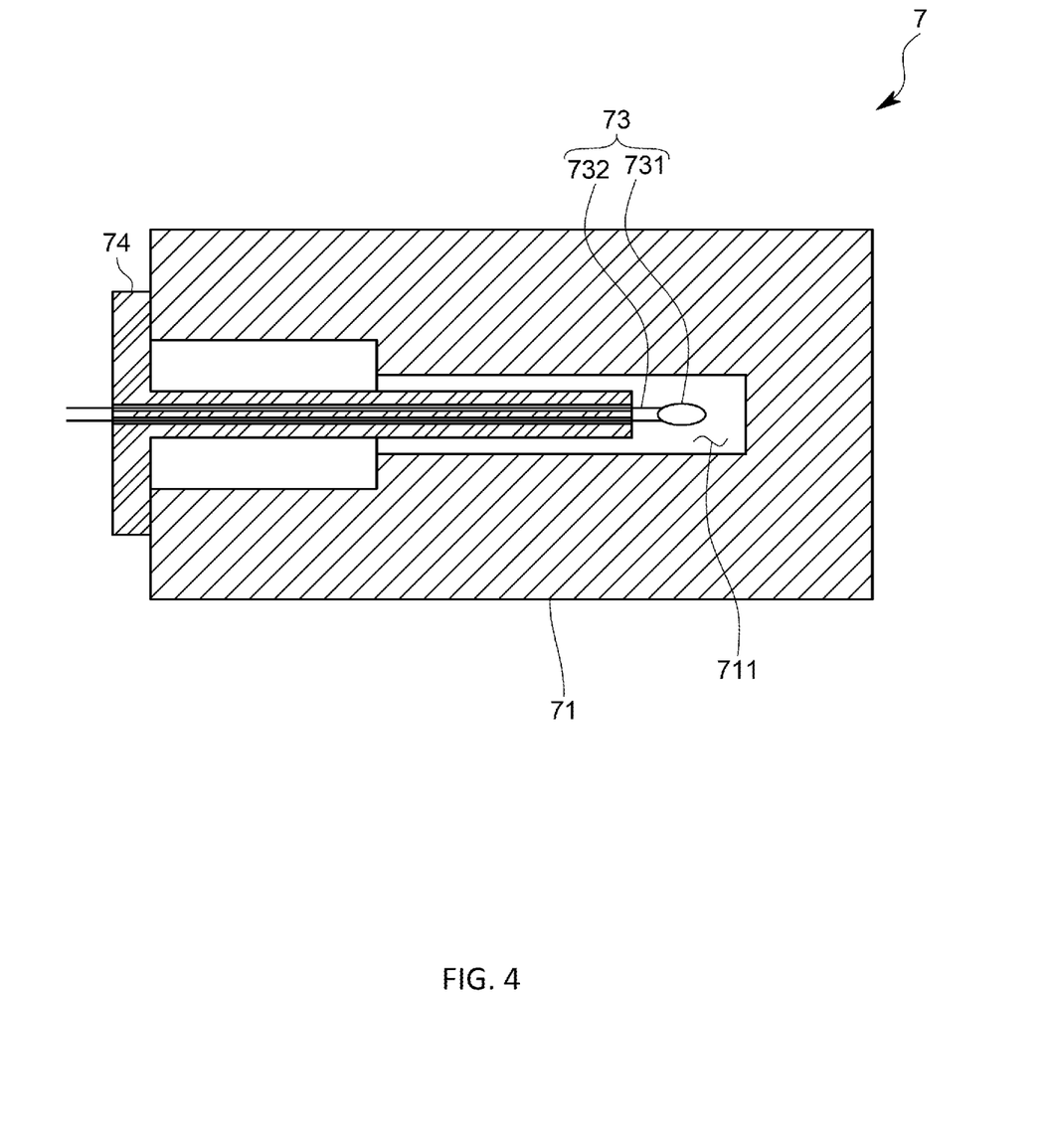
FIG. 4 is a schematic sectional view illustrating an internal structure of a temperature control mechanism according to the embodiment.

The temperature control mechanism 7 accommodates and holds the plurality of specimen tubes FC, for example, in a matrix. The temperature control mechanism 7 includes a metallic (for example, aluminum) holder block 71 that holds the specimen tubes FC, a heater 72 or the like as a heat source provided in the holder block 71, and a thermistor 73 that detects a temperature of the holder block 71. On the basis of the temperature detected by the thermistor 73, the heater 72 as the heat source is controlled by a controller COM such that the temperature of the holder block 71 becomes a predetermined temperature. As shown in FIG. 4, the holder block 71 is provided with an insertion hole 711 having a substantially two-stage cylindrical shape for inserting the thermistor 73 therein, and a temperature sensor 731 at a distal end of the thermistor 73 is disposed to a depth of the insertion hole 711. Specifically, two lead wires connected to the temperature sensor 731 of the thermistor 73 are inserted into an insertion body 74 having a shape in which a base end has a disk shape and a thin cylinder protrudes from a center of the base end, and the temperature sensor 731 is exposed from a distal end of the insertion body 74. In this state, the insertion body 74 is inserted into the insertion hole 711, and a contact surface of a disk-shaped portion of the insertion body 74 is brought into contact with a periphery of an opening of the insertion hole 711. In this way, the temperature sensor 731 of the thermistor 73 can be always positioned at the same position even when the insertion hole 711 is deep. Further, the insertion body 74 is fixed by a sealing material such as resin in the insertion hole 711.

In the reagent setting part 8, the reagent container RC1 storing a pretreatment reagent for subjecting a specimen to a pretreatment and the reagent container RC2 storing the luminescent reagent are set. Examples of the pretreatment reagent include an ATP scavenging solution that scavenges ATP (free ATP) other than living cells (viable bacteria) contained in the specimen, and an ATP extract for extracting ATP from living cells.

Figure 5:
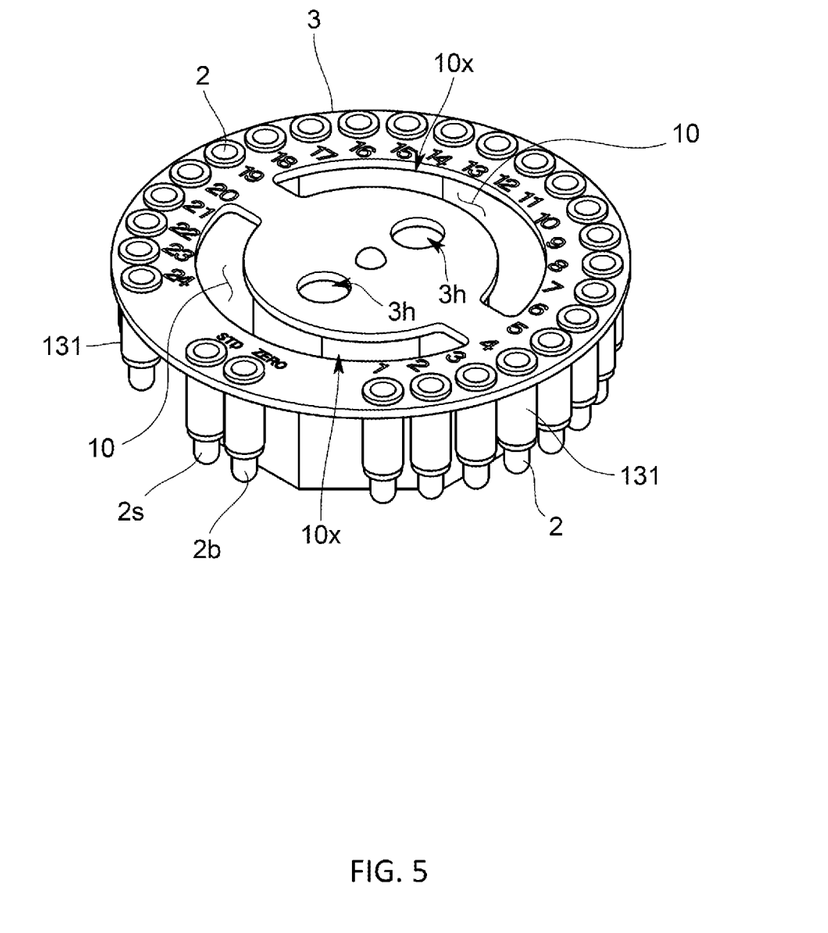
FIG. 5 is a perspective view illustrating a holder holding a plurality of containers according to the embodiment.

The holder 3 is provided so as to be rotatable with respect to the device body 101, and holds the plurality of containers 2 on an identical circumference about a predetermined rotation center, in particular, as illustrated in FIG. 5. In addition to the plurality of containers 2 for sample measurement, the holder 3 according to the embodiment holds a container 2b for blank measurement and a container 2s for standard solution measurement. In the holder 3, a disposal box 10 as a disposal tip storage for disposing the pipette tips PT of the dispensing mechanism 6 is integrally provided on an inner side of the plurality of containers 2. The disposal box 10 has an arc-shaped opening 10x in plan view. Further, the holder 3 is attachable to and detachable from the device body 101, and a plurality of (two in this case) holding holes 3h for holding are formed in order to facilitate attaching and detaching operation. The holding holes 3h are through holes for inserting fingers and holding, and are provided on an inner side of the opening 10x of the disposal box 10. The holding holes 3h are provided on the inner side of the opening 10x in this manner, and this can prevent a hand from inadvertently touching the discarded pipette tip PT when the holder 3 is held. In the embodiment, the holder 3 includes metal, and is configured not to be charged by friction or the like when fingers are inserted.

As illustrated in FIG. 1, the photodetector 4 detects light emitted from the sample in the container 2 held by the holder 3, and is, for example, a photomultiplier tube (PMT) in the embodiment. The photodetector 4 is provided below the container 2 held by the holder 3. An optical system 12 having a reflector 11 for guiding light emitted from the sample in the container 2 to the photodetector 4 is provided above the photodetector 4. The reflector 11 is movable forward and backward with respect to the container 2 located above the reflector 11. The light emitted from the sample into the container 2 can be efficiently guided to the photodetector 4 by bringing the reflector 11 close to the container 2, and the container 2 can be prevented from moving by retracting the reflector 11 from the container 2. In the embodiment, the optical system 12 and the photodetector 4, including the reflector 11, may also be movable forward and backward with respect to the container 2.

In the embodiment, as illustrated in FIG. 1, not only the photodetector 4 but also a neutralizer NE that neutralizes the container 2 is provided below the holder 3. The neutralizer NE supplies negative ions and positive ions from below the container 2 to neutralize the container 2. Since the neutralizer NE supplies both negative ions and positive ions in this manner, the container 2, which is charged positively or negatively, can be still reliably neutralized. A timing of supplying negative ions and positive ions may be same or different. As described above, the biological sample analysis apparatus 100 can prevent occurrence of a discharge phenomenon due to static electricity by reliably neutralizing the containers 2. Therefore, the biological sample analysis apparatus 100 can prevent detection of light due to a discharge phenomenon and occurrence of a measurement error.

The neutralizer NE is provided apart from the photodetector 4 by a predetermined arc length in a circumferential direction as an arrangement direction of the containers 2. In the embodiment, the neutralizer NE is disposed opposite to the photodetector 4 about a rotation center of the holder 3. That is, the neutralizer NE is disposed at a position farthest from the photodetector 4 on a circumference on which the containers 2 are arranged. In the embodiment, each container 2 is neutralized by the neutralizer NE, and then is positioned at a detection position Xdet by rotation of the holder 3. This configuration can prevent ions supplied from the neutralizer NE from being detected by the photodetector 4 while the containers 2 are neutralized.

The holder drive mechanism 5 moves the holder 3 to sequentially position each container 2 held by the holder 3 at the detection positions Xdet detected by the photodetector 4. Specifically, as illustrated in FIG. 1, the holder drive mechanism 5 includes an installation base 51 on which the holder 3 is installed, a rotation shaft 52 for rotating the holder 3 installed on the installation base 51, and an actuator 53 for rotating the rotation shaft 52. In addition, the holder drive mechanism 5 is provided with a rotational position sensor (not illustrated) that detects a rotational position of the holder 3. On the basis of a detection signal of the rotational position sensor, the actuator 53 is rotationally controlled by the controller COM so as to position the container 2 to be measured at the detection position Xdet.

Figure 6:
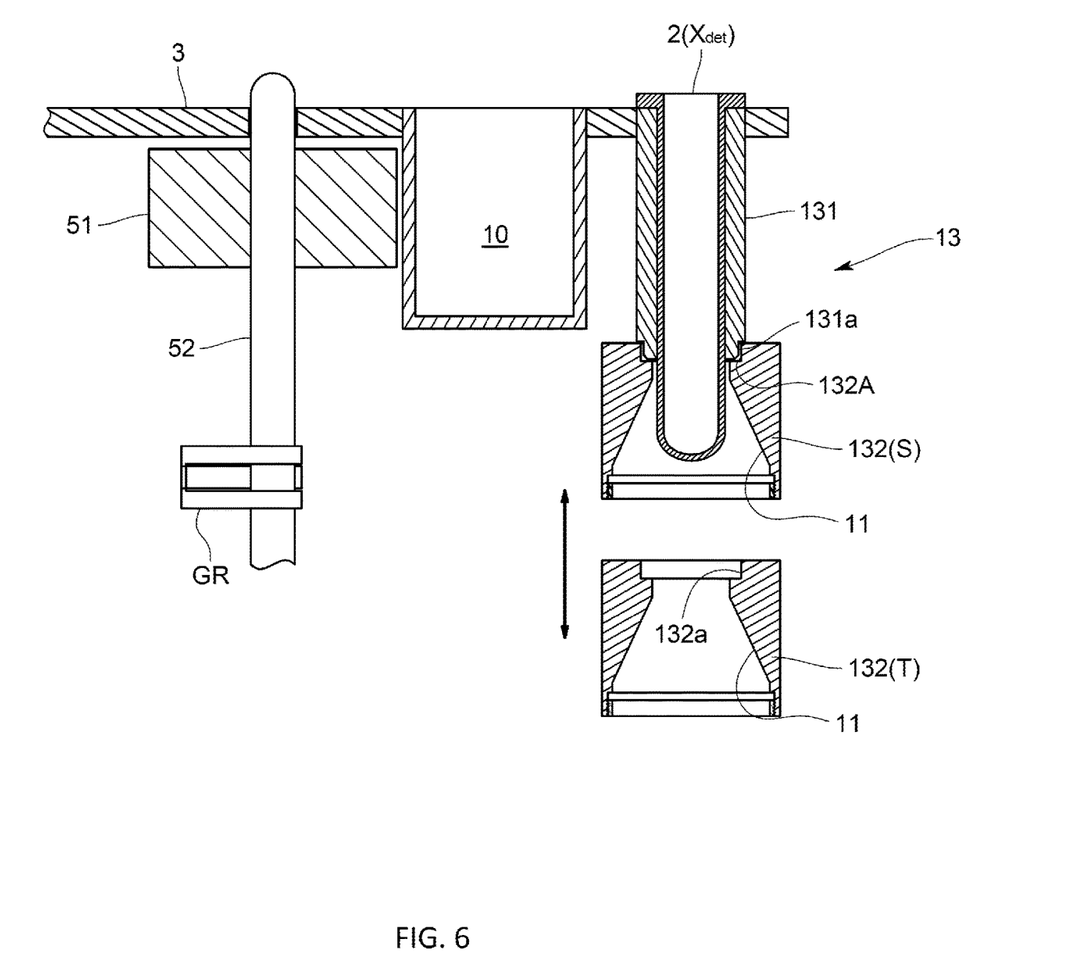
FIG. 6 is a schematic diagram illustrating each position and a structure of a periphery of a movable-side light shield of a light shielding mechanism according to the embodiment.
Figure 7:
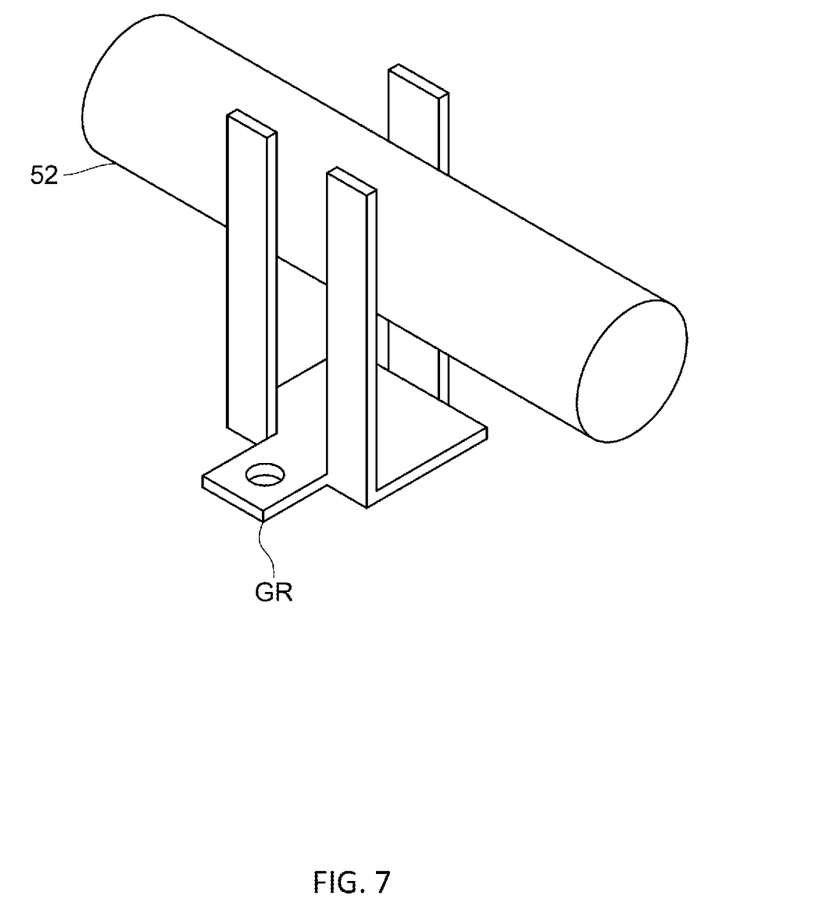
FIG. 7 is a schematic perspective view illustrating a structure of a ground member according to the embodiment.

In the embodiment, the holder 3 is electrically connected to the rotation shaft 52 via the installation base 51. Thus, the installation base 51 and the rotation shaft 52 include metal. As illustrated in FIGS. 6 and 7, an electric charge of holder 3 is connected to a ground by a ground member GR attached to the rotation shaft 52. Specifically, the ground member GR is a three-claw leaf spring member that clamps a side surface of the rotation shaft 52. Each claw provided so as to sandwich the rotation shaft 52 is biased to be pressed inward. Since each claw is in line contact with the rotation shaft 52 and is biased inward in this manner, when wear occurs between the rotation shaft 52 and the ground member GR, a state of line contact can be substantially maintained, and the charge accumulated in the holder 3 can be continued to flow to the ground.

As illustrated in FIGS. 1 to 3, the dispensing mechanism 6 includes a nozzle 61 for sucking or discharging a sample or each reagent, a pump mechanism 62 such as a syringe that drives suction or discharge of the nozzle 61 through a flow path connected to the nozzle 61, and a nozzle moving mechanism 63 that moves the nozzle 61 in a predetermined direction.

The nozzle 61 includes a tip holder 611 that holds so as to be attachable and detachable to and from the pipette tip PT that contacts and holds the sample and each reagent. The tip holder 611 is provided with an internal flow path, a base end to which a flow path is connected, and a distal end opening to which the pipette tip PT is connected. The pipette tip PT is wet in the tip holder 611.

The nozzle moving mechanism 63 linearly moves the nozzle 61 in a horizontal direction (an X-axis direction and a Y-axis direction) and linearly moves the nozzle 61 in a vertical direction (a Z-axis direction). Specifically, the nozzle moving mechanism 63 includes a movable member 631 that holds the nozzle 61, a slide mechanism 632 provided in each of the X-axis direction, the Y-axis direction, and the Z-axis direction, and an actuator 633 that moves the movable member 631 in each direction along the slide mechanism 632. The actuator 633 and the pump mechanism 62 are controlled by the controller COM to perform each operation in the ATP measurement.

As illustrated in FIG. 6, the biological sample analysis apparatus 100 according to the embodiment includes the light shielding mechanism 13 that guides light exiting from the sample in the container 2 located at the detection position Xdet to the photodetector 4 and prevents the light exiting from the sample in the other containers 2 (specifically, the containers 2 having been measured) from being guided to the photodetector 4.

The light shielding mechanism 13 includes a container-side light shield 131 provided on each container 2, and a movable-side light shield 132 that moves forward and backward with respect to the container 2 located at the detection position Xdet.

The container-side light shield 131 includes a member having no light permeability, and covers an upper part of each container 2. Specifically, the container-side light shield 131 covers an entire circumference of the upper part of each container 2. In the embodiment, the container-side light shield 131 having a cylindrical shape is provided in a container holding part of the holder 3, the container-side light shield 131 accommodates the container 2, and the container-side light shield 131 covers the entire circumference of the upper part of the container 2 held by the holder 3.

The movable-side light shield 132 includes a member having no light permeability, and covers a lower part of the container 2 located at the detection position Xdet except for the upper part of the container 2 covered by the container-side light shield 131. Specifically, the movable-side light shield 132 covers the entire circumference of the lower part of the container 2 located at the detection position Xdet. The movable-side light shield 132 moves up and down between a light shielding position S that covers the lower part of the container 2 located at the detection position Xdet and a retraction position T that is spaced downward apart from the lower part of the container 2. Note that the movable-side light shield 132 moves up and down, for example, by a lifting device 14 using an actuator. The lifting device 14 is controlled by the controller COM in conjunction with operations of the holder drive mechanism 5 and the dispensing mechanism 6.

A first step 131a is formed over the entire circumference at a lower end of the container-side light shield 131, and a second step 132A corresponding to the first step 131a is formed over the entire circumference at an upper end of the movable-side light shield 132. Then, in a state where the movable-side light shield 132 is at the light shielding position S, the first step 131a of the container-side light shield 131 and the second step 132A of the movable-side light shield 132 are engaged with each other to cover both the upper and lower parts of the container 2 located at the detection position Xdet. As described above, the first step 131a and the second step 132A are engaged with each other to further ensure light shielding. Any one of the steps 131a or 132A may have a groove shape.

When the luminescent reagent is introduced into the sample in the container 2 by the dispensing mechanism 6, the movable-side light shield 132 is at the light shielding position S. When the measurement of light emission is completed and the container 2 at the detection position Xdet is switched, the movable-side light shield 132 is at the retraction position T.

The movable-side light shield 132 according to the embodiment constitutes the reflector 11 that guides light emitted from the sample in the container 2 located at the detection position Xdet to the photodetector 4.

Figure 8:
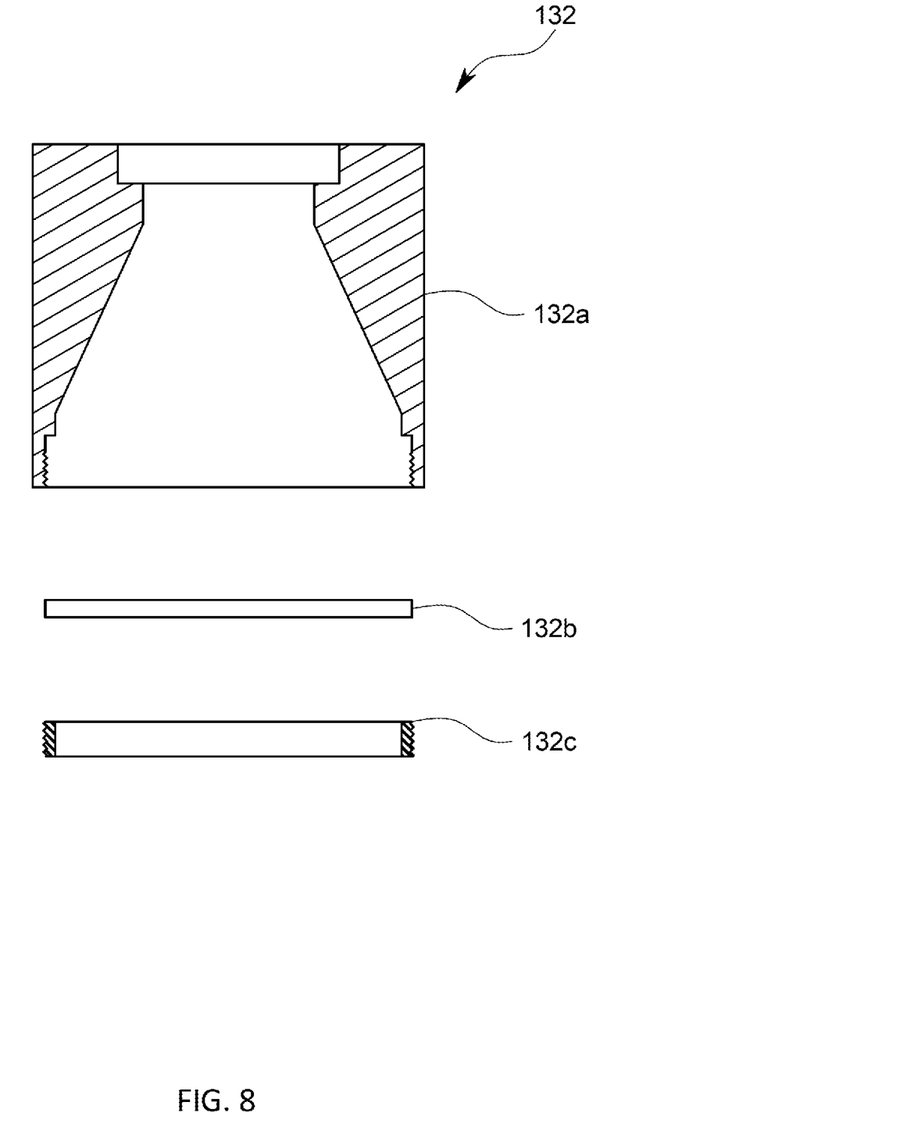
FIG. 8 is a schematic exploded sectional view illustrating a structure of a movable-side light shield according to the embodiment.

Specifically, as illustrated in FIGS. 6 and 8, the movable-side light shield 132 includes a reflector body 132a that covers the distal end of the container 2, a glass plate as a light transmitting plate 132b provided in the reflector body 132a, and a pressing member 132c that is attachable to and detachable from the reflector body 132a and presses and fixes the light transmitting plate 132b to the reflector body 132a.

The reflector body 132a is a cylindrical body whose inner surface is mirror-finished, for example, and has a tapered inner peripheral surface formed so as to gradually expand downward from an upper end opening. A step is formed at a distal end of the reflector body 132a, and the light transmitting plate 132b is pressed against the step. An internal screw is cut at the distal end of the reflector body 132a.

The light transmitting plate 132b has a substantially disk shape, and has an outer diameter substantially equal to an inner diameter of the distal end of the reflector body 132a. The pressing member 132c has a substantially ring shape, and has an outer peripheral surface on which an external screw screwed with the internal screw formed at the distal end of the reflector body 132a is cut. A reflective film is provided on an inner peripheral surface of the pressing member 132c, and thus light that has passed through the light transmitting plate and has reached the inner peripheral surface of the pressing member is also guided to the photodetector 4. In the movable-side light shield 132, the light transmitting plate 132b is attachable to and detachable from the reflector body 132a in this manner, and thus, the light transmitting plate 132b, onto which water droplets or dirt adhere, for example, can be easily cleaned and maintained. Further, the inner peripheral surface of the pressing member 132c, which is provided with the reflective film, can prevent light generated in the sample from being lost in this part.

In this manner, the reflector 11 facing toward the photodetector 4 is formed on an inner surface of the movable-side light shield 132. The reflector 11 can guide the light exiting from a side wall of the container 2 located at the detection position Xdet toward the photodetector 4 without leaking.

<Analysis Method>

Next, an analysis method will be described together with operation of the biological sample analysis apparatus 100 configured as described above.

For example, a large volume (for example, 50 ml to 200 ml) of a specimen is concentrated to a predetermined amount (for example, 1 μl to 1,000 μl) to generate a sample. The specimen tube FC storing the sample is set in the temperature control mechanism 7 of the device body 101. The holder block 71 of the temperature control mechanism 7 is controlled to have a constant temperature by the heater 72. The cover 102 is closed in a state where a predetermined number of specimen tubes FC are set, and measurement is started. Although each container 2 held by the holder 3 in this state is empty, a standard solution having a known ATP amount is stored in the container 2 for standard solution measurement.

When the measurement is started, the controller COM controls the dispensing mechanism 6 to dispense each pretreatment reagent into each of the specimen tubes FC held by the temperature control mechanism 7 in accordance with a predetermined sequence. As a result, the sample in the specimen tube FC is subjected to a predetermined pretreatment (ATP extraction). Thereafter, the dispensing mechanism 6 introduces the pretreated sample in each of the specimen tubes FC into each of the containers 2 held by the holder 3.

Then, the controller COM controls the holder drive mechanism 5 to move the container 2 to be measured to the detection position Xdet. In this process, ions are supplied to the container 2 passing over the neutralizer NE, and the container 2 is neutralized. After moving the container 2 to be measured to the detection position Xdet, the controller COM controls the lifting device 14 to move the movable-side light shield 132 of the light shielding mechanism 13 to the light shielding position S. After this state, the controller COM controls the dispensing mechanism 6 to introduce the luminescent reagent into the container 2 located at the detection position Xdet. As a result, light emitted from the sample in the container 2 located at the detection position Xdet is detected by the photodetector 4. A light intensity signal obtained by the photodetector 4 is subjected to arithmetic processing by the controller COM to calculate an ATP amount (amol). Among light intensity signals obtained by the photodetector 4, an integrated signal for a predetermined time (for example, several seconds) from a time point when the luminescent reagent is introduced is used for the arithmetic processing.

After luminescence measurement of one container 2 is completed, the controller COM controls the lifting device 14 to move the movable-side light shield 132 of the light shielding mechanism 13 to the retraction position T, and then controls the holder drive mechanism 5 to move the next container 2 to be measured to the detection position Xdet. In this way, the luminescence measurement of the sample in each container 2 is sequentially performed. Before the luminescence measurement of each container 2, blank measurement and standard solution measurement are performed, and zero point calibration and span calibration are performed.

After the measurement is completed for all the samples in this manner, the cover 102 is opened to replace the specimen tube FC held by the temperature control mechanism 7, and the container 2 held by the holder 3 is replaced. Here, when the container 2 held by the holder 3 is replaced, the holder 3 is removed from the device body 101 by holding the holding hole 3h of the holder 3. The used and discarded pipette tip PT is in the disposal box 10 of the holder 3 in the holder 3, and thus the discarded pipette tip PT can also be taken out from the device body 101 at the same time by removing the holder 3 from the device body 101.

<Effects of Embodiment>

In the biological sample analysis apparatus 100 according to the embodiment configured as described above, the container 2 is neutralized by the neutralizer NE, and it is therefore possible to prevent the container 2 from being charged and discharged due to static electricity and prevent discharge light emission from being detected by the photodetector 4 to cause a measurement error. Further, since the container 2 is neutralized, it is possible to prevent a state in which part of the sample is attracted by static electricity and adheres to an inner wall surface of the container 2 as a droplet, and part of the sample does not react with the reagent.

As a result, a minute luminescence intensity can be detected, and calculation accuracy of the ATP amount (amol) can be improved as compared with the related art.

The dispensing mechanism 6 introduces the reagent into the container 2 at the detection position Xdet, and this makes it possible to detect light without leakage at a time point when light emission is started. Here, before the reagent is introduced by the dispensing mechanism 6, the light exiting from the sample in the container 2 other than the container 2 located at the detection position Xdet is shielded by the light shielding mechanism 13, and thus the light can be accurately detected at the time point when the light emission is started.

The light shielding mechanism 13 is divided into the container-side light shield 131 fixed close to the container 2 and the movable-side light shield 132 movable with respect to the container 2, and this configuration eliminates the need for covering all of the container 2 with a movable member. As a result, the movable member of the light shielding mechanism 13 can be made compact, and the configuration can be simplified.

The movable-side light shield 132 constitutes the reflector 11 guiding the light emitted from the sample in the container 2 located at the detection position Xdet to the photodetector 4, and thus the light emitted from the sample can be efficiently guided to the photodetector 4. Here, the reflective film is also provided on the pressing member 132c on the distal end of the light transmitting plate 132b, and this configuration can further reduce a loss of light emitted from the sample.

The light shielding mechanism 13 covering the entire circumference of the container 2 located at the detection position Xdet can shield not only light emitted from the container 2 other than the container 2 located at the detection position Xdet as much as possible but also other stray light, and thus can further reduce noise.

Other Embodiments

Note that the present invention is not limited to the above embodiment.

For example, the holder 3 holds the plurality of containers 2 on an identical circle, but may hold the plurality of containers 2 along a predetermined direction in a matrix or the like. In this case, it is conceivable that the holder drive mechanism 5 is configured to linearly move the holder 3 in the horizontal direction (the X-axis direction and the Y-axis direction).

In this case, it is sufficient that the neutralizer NE supplies ions to a movement path of the container 2. Further, the neutralizer NE is not limited to supplying ions from below the container 2, and for example, may supply ions from a side surface of the container 2 for neutralization.

The biological sample analysis apparatus 100 for rapid microbiological test of the present invention is not limited to the ATP amount measurement device as described in the embodiment. Specific examples of the rapid microbiological test include a bioluminescence method and a fluorescence method for measuring ATP or the like, an immunological method for measuring an antigen, and solid phase cytometry, flow cytometry for measuring bacterial cells or the like. The biological sample analysis apparatus 100 for rapid microbiological test of the present invention can also measure a *mycoplasma* and endotoxin.

In addition, various modifications and combinations of some of the embodiments may be made without departing from the gist of the present invention.

INDUSTRIAL APPLICABILITY

The present invention can provide a biological sample analysis apparatus capable of preventing a container storing a sample from being charged and of measuring only a luminescence intensity of light emitted from the sample accurately.

The invention claimed is:

1. A biological sample analysis apparatus for rapid microbiological test, the biological sample analysis apparatus analyzing light generated by a biological origin substance contained in a sample, the biological sample analysis apparatus comprising:
  a holder that holds a plurality of containers, each of the containers storing the sample;
  a photodetector fixed at a predetermined position and provided below the containers;
  a holder drive mechanism that drives the holder and sequentially positions each of the containers held by the holder at a detection position detected by the photodetector;
  a neutralizer that neutralizes the containers held by the holder and is provided below the holder, wherein
  the neutralizer comprises a supply of positive ions and negative ions, and supplies the positive ions and the negative ions to the containers from below the holder, thereby eliminating static electricity from the containers,
  the photodetector detects light emitted from the sample in each of the containers from below the holder,
  the holder is rotatable about a predetermined rotation center and holds the plurality of containers on an identical circumference about the rotation center, and
  the neutralizer is disposed opposite to the photodetector about the rotation center of the holder in a circumferential direction in which the plurality of containers are arranged.

2. The biological sample analysis apparatus according to claim 1, wherein
  each of the containers has a substantially tubular shape and has a distal end that is exposed downward from the holder.

3. The biological sample analysis apparatus according to claim 1, wherein the holder includes a conductor.

4. The biological sample analysis apparatus according to claim 1, wherein the holder is electrically connected to the holder drive mechanism and connected to a ground.

5. The biological sample analysis apparatus according to claim 1, wherein
  the holder drive mechanism includes a rotation shaft connected to the holder, and
  the holder drive mechanism further includes a ground member that clamps a side surface of the rotation shaft.

6. The biological sample analysis apparatus according to claim 1, further comprising a dispensing mechanism that introduces, into the containers, a reagent that reacts with the biological origin substance and generates light, wherein
  the dispensing mechanism is attachable to and detachable from a pipette tip that is in contact with the reagent, and
  the pipette tip is wet before being used.

7. The biological sample analysis apparatus according to claim 1, further comprising a light shielding mechanism provided on each of the containers and including a container-side light shield that covers an upper part of each of the containers and a movable-side light shield that moves forward and backward with respect to each of the containers located at the detection position and covers a lower part of each of the containers located at the detection position, wherein the container-side light shield and the movable-side light shield include metal.

8. The biological sample analysis apparatus according to claim 7 wherein
  the movable-side light shield includes
  a reflector body that covers a distal end of each of the containers,
  a light transmitting plate provided in the reflector body, and
  a pressing member that is attachable to and detachable from the reflector body and presses and fixes the light transmitting plate to the reflector body.

9. The biological sample analysis apparatus according to claim 8, wherein the pressing member has a substantially ring shape attached in the reflector body and has an inner peripheral surface provided with a reflective film.

10. The biological sample analysis apparatus according to claim 1, further comprising a temperature control mechanism including
  a holder block that holds a specimen tube storing the sample before being dispensed into the containers, and
  a heat source provided in the holder block,
  a thermistor that includes a temperature sensor and a lead wire connected to the temperature sensor and measures a temperature of the holder block,
  an accommodating hole provided in the holder block and configured to accommodate the thermistor inside, and an insertion body that covers a lead wire of the thermistor and is inserted into the accommodating hole, wherein the insertion body has an abutment surface that abuts on a periphery of an opening of the accommodating hole at a base end of the insertion body.

11. A biological sample analysis method using a biological sample analysis apparatus for rapid microbiological test, wherein the biological sample analysis apparatus includes a holder that holds a plurality of containers storing a sample, a photodetector fixed at a predetermined position, holder drive mechanism that drives the holder and sequentially positions each of the containers held by the holder at a detection position detected by the photodetector, and a neutralizer comprising a supply of positive ions and negative ions, the method comprising:

supplying, via the neutralizer, the positive ions and the negative ions to the containers from below the holder, and neutralizing the containers held by the holder, thereby eliminating static electricity from the containers;

detecting, via the photodetector, light emitted from the sample in each of the containers from below the holder; and analyzing the light generated by a biological origin substance contained in the sample, wherein the holder is rotatable about a predetermined rotation center and holds the plurality of containers on an identical circumference about the rotation center, and the neutralizer is disposed opposite to the photodetector about the rotation center of the holder in a circumferential direction in which the plurality of containers are arranged.

12. The biological sample analysis apparatus according to claim 1, wherein each of the containers has a substantially tubular shape and has a distal end that is exposed downward from the holder, and the neutralizer neutralizes the distal end of each of the containers that is exposed downward from the holder by supplying the positive ions and the negative ions from below the holder to the distal end of each of the containers that is exposed downward from the holder.

* * * * *

UNITED STATES PATENT AND TRADEMARK OFFICE
CERTIFICATE OF CORRECTION

PATENT NO. : 12,398,414 B2
APPLICATION NO. : 17/595825
DATED : August 26, 2025
INVENTOR(S) : Hideki Nakayama et al.

Page 1 of 1

It is certified that error appears in the above-identified patent and that said Letters Patent is hereby corrected as shown below:

In the Claims

Column 13, Line 10, delete "holder" and insert --a holder--.

Signed and Sealed this
Tenth Day of February, 2026

John A. Squires
*Director of the United States Patent and Trademark Office*